United States Patent [19]

Boothe et al.

[11] Patent Number: 4,764,365

[45] Date of Patent: Aug. 16, 1988

[54] PERSONAL SKIN CARE PRODUCTS CONTAINING DIMETHYL DIALLYL AMMONIUM CHLORIDE/ACRYLIC ACID-TYPE POLYMERS

[75] Inventors: Jerry E. Boothe, Coraopolis; Lewis D. Morse, Pittsburgh, both of Pa.; William L. Klein, Nutley, N.J.

[73] Assignee: Calgon Corporation, Pittsburgh, Pa.

[21] Appl. No.: 923,529

[22] Filed: Oct. 27, 1986

[51] Int. Cl.$^4$ .......................... A61K 7/00; A61K 7/15; A61K 7/50; A61K 7/32

[52] U.S. Cl. .......................... 424/81; 424/59; 424/63; 424/65; 424/73; 252/DIG. 5; 252/DIG. 16; 514/846

[58] Field of Search .......................... 424/59, 65, 73, 81; 514/846, 315; 252/117, 368, 547, DIG. 2, DIG. 5, DIG. 13, DIG. 16, DIG. 3

[56] References Cited

U.S. PATENT DOCUMENTS

| | | | |
|---|---|---|---|
| Re. 28,543 | 9/1975 | Boothe et al. | 428/514 |
| 3,761,417 | 9/1973 | Parran | 424/78 X |
| 3,769,398 | 10/1973 | Hewitt | 424/78 X |
| 3,912,808 | 10/1975 | Sokol | 424/70 X |
| 3,986,825 | 10/1976 | Sokol | 424/70 X |
| 3,996,146 | 12/1976 | Tarasov et al. | 424/DIG. 2 X |
| 4,027,008 | 5/1977 | Sokol | 424/70 X |
| 4,040,984 | 8/1977 | Sharpe, Jr. et al. | 524/521 X |
| 4,329,335 | 5/1982 | Su et al. | 424/71 X |
| 4,348,380 | 9/1982 | Jacquel et al. | 424/65 X |
| 4,401,650 | 8/1983 | Salamone | 424/81 |
| 4,491,539 | 1/1985 | Hoskins et al. | 252/DIG. 5 X |
| 4,578,216 | 3/1986 | Fujii et al. | 252/DIG. 13 X |
| 4,673,525 | 6/1987 | Small et al. | 252/117 X |
| 4,673,571 | 6/1987 | Mahieu et al. | 424/65 X |

*Primary Examiner*—John E. Kittle
*Assistant Examiner*—Susan S. Rucker
*Attorney, Agent, or Firm*—W. C. Mitchell; M. C. Sudol, Jr.

[57] ABSTRACT

This invention relates to improved personal skin care products which contain dimethyl diallyl ammonium chloride/acrylic acid-type polymers. These polymers provide exceptional feel to skin when personal skin care products containing them, such as hand and face lotions, soaps or creams, suntan lotions, bubble baths, shaving creams, antiperspirants, and deodorants, are used.

8 Claims, No Drawings

PERSONAL SKIN CARE PRODUCTS CONTAINING DIMETHYL DIALLYL AMMONIUM CHLORIDE/ACRYLIC ACID-TYPE POLYMERS

BACKGROUND OF THE INVENTION

The instant invention relates to improved personal skin care products which contain at least one dimethyl diallyl ammonium chloride (DMDAAC)/acrylic acid-type polymer. These polymers impart a soft, silky feel to the skin when present at low concentrations and are compatible with anionic systems.

Numerous references disclose cosmetic and personal care compositions such as shampoos, antiperspirant formulations, anti-dandruff rinse conditioners, etc., which contain anionic and/or cationic polymers, an active agent, surfactants, emollients and other additives and preservatives commonly employed in the industry. Pertinent references which relate to DMDAAC/acrylic acid polymers or which disclose cosmetic and personal care formulations containing anionic and cationic polymers include:

1. U.S. Pat. No. 3,761,417, which is directed to detergent compositions containing particle deposition enhancing agents. More particularly, this patent discloses detergent and personal use toilet detergent bars containing water-soluble particles such as antimicrobial agents, organic surfactants and cationic polymers. Surfactants are an essential ingredient of these compositions, and DMDAAC is mentioned as a possible cationic polymer.
2. U.S. Pat. No. 3,769,398, which discloses non-ionic hair shampoo formulations containing an active ingredient such as a betaine, sulfo betaine, amine oxide or mixture thereof, a water soluble polymer such as a polyethyleneimine-ethylene oxide or propylene oxide polymer or a propoxylated polyethyleneimine.
3. U.S. Pat. No. 4,329,335, which describes an amphoteric, nonionic anti-dandruff shampoo containing an active agent (1-imidazalyl-1-) (chlorophenoxy-3,3-dimethylbutane-2-one) and amphoteric surfactants. DMDAAC is disclosed as a preferred quaternized ammonium compound in this patent.
4. Published European Patent Application No. 74,819, which discloses an anti-dandruff cream rinse conditioner containing zinc pyrithione, glucan or guar gum, hydroxyethyl cellulose and a homopolymer of DMDAAC or a copolymer of DMDAAC and acrylamide.
5. U.S. Pat. No. 3,996,146, which discloses a shampoo formulation comprising from 0.05 to about 2.5%, by weight, of a cationic resin including quaternary polymers derived from dimethyl diallyl ammonium salts.
6. U.S. Pat. No. 4,040,984, which discloses polymers useful for preparing electroconductive paper which comprise quaternary diallyl dialkyl ammonium monomers and acrylic acid.
7. U.S. Pat. No. 3,912,808, which discloses a composition and method for waving or straightening hair using an aqueous solution of a reducing agent and a water soluble secondary or tertiary amine polymer or a polymer of diallyl amine or a quaternary polymer of diallyl dialkyl ammonium salts. This patent also discloses the use of dialkyl ammonium polymers which contain acrylamide or diacetone acrylamide. The use of dimethyl diallyl ammonium chloride/acrylic acid polymers is not disclosed or suggested.
8. U.S. Pat. No. 4,027,008, which discloses hair treating compositions which contain a water soluble secondary or tertiary amine polymer or a polymer of diallyl amine or a quaternary polymer of diallyl dialkyl ammonium salts. This patent does not disclose or suggest the use of DMDAAC/acrylic acid polymers, and states that many widely used products for treating hair contain anionic surfactants which may inactivate cationic additives.
9. U.S. Pat. No. 3,986,825, which discloses the use of dialkyl diallyl ammonium polymers in cosmetic products, including copolymers of a dialkyl diallyl ammonium monomer and acrylamide or diacetone acrylamide. However, polymers containing these cationic moieties and acrylic acid are not disclosed or suggested.

In summary, though dialkyl diallyl ammonium polymers are widely used in cosmetic applications, the use of polymers containing a diallyl dialkyl ammonium monomer and acrylic acid is not known or suggested in the art. These polymers provide an increased level of cationic activity with unexpected compatibility in anionic systems.

DETAILED DESCRIPTION OF THE INVENTION

The instant invention is directed to a method for improving the feel of a personal skin care product, comprising adding to said product an effective amount of a polymer comprising:

(a) about 60 to 99%, based on total polymer weight, of a quaternary diallyl dialkyl ammonium monomer, wherein alkyl groups are independently selected from alkyl groups of 1 to 18 carbon atoms, preferably $C_{1-4}$ alkyl, and wherein said quaternary diallyl dialkyl ammonium monomer's counterion is selected from the group consisting of conjugate bases of acids having an ionization constant greater than $10^{-13}$, more preferably, selected from the group consisting of fluoride, bromide, chloride, hydroxide, nitrate, acetate, hydrogen sulfate, and primary phosphates; and (b) about 1 to about 40%, based on total polymer weight, of an anionic monomer selected from the group consisting of acrylic acid and methacrylic acid; wherein the weight average molecular weight of said polymer ranges from about 50,000 to about 10,000,000, as determined by gel permeation chromatography.

The instant invention is also directed to improved personal skin care products which contain the above described polymer.

As used herein, the phrase "personal skin care product" includes, but is not limited to, hand and face lotions, soaps and creams, suntan lotions, bubble baths, shaving creams, antiperspirants and deodorants. The instant polymers impart a soft and silky feel to the skin when products containing them are used. The term "feel", as used herein, refers to a subjective measure of the smoothness and silkiness that a personal skin care product imparts to the skin when applied to the skin.

Personal skin care products generally comprise an active agent, such as a detergent or surfactant, conditioner, emollient, antimicrobial, antiperspirant and moisturizing agent. For example, active agents may include antimicrobial agents such as trichlorocarban (3,4,4′-trichloro carbanilide), triclosan (2,4,4′-trichloro carbonilide), triclosan (2,4,4′-trichloro-2′-hydroxy diphenyl ether), benzalkonium chloride, zinc phenosulfonate, zinc ricinoleate and the like.

Commonly used anti-perspirants include aluminum zirconium complex, aluminum chlorohydrate and the like.

Representative emollients, humectants and moisturizing agents include $C_{12}$–$C_{15}$ alcohol benzoates, sorbitol, glycerin, propylene glycol (PEG), lanolin, vegetable oils, mineral oils, isopropyl myristate, aloe vera, jojoba oil and the like.

Other cosmetically acceptable excipients that a personal care product formulation may contain are thickening agents, buffering agents and preservatives. Suitable water soluble preservatives are sodium bisulfite, sodium thiosulfate, ascorbate, benzalkonium chloride, glydant chlorobutanol, thimerosal, phenylmercuric borate, Dowicil 200 parabens, Tektamer 38(1,2-dibromo-2,4-dicyanobutane), benzyl alcohol, phenylethanol and the like. Suitable thickening agents are Cab-O-Sil M5 made by Cabot Corporation, sodium stearate, magnesium aluminum silicate, hydroxyethyl cellulose and the like. These agents may be present in amounts of from 0.05 to 50% by weight and preferably 1 to 5%. Suitable water soluble buffering agents are alkali or alkali earth carbonates, phosphates, bicarbonates, citrates, borates, acetates, acid anhydrides, succinates and the like, such as sodium phosphate, citrate, borate, acetate, bicarbonate and carbonate. These agents may be present in an amount sufficient to maintain some optimum pH of the system in the range 2 to 9. As such, the buffering agent can be as much as 20%, on a weight basis, of the total composition. Additional active agents are fully described in U.S. Pat. No. 3,986,825, which is incorporated herein by reference.

The instant polymers, in addition to imparting improved feel to skin, may enhance dispersion and improve the efficacy of functional ingredients in personal skin care products.

As used herein, the term "effective amount" refers to that amount of polymer required to improve the feel of the personal skin care product to which it is added. Generally, the instant polymers are added at a dosage ranging from about 0.1% active polymer solids to about 5% active polymer solids, based on the total weight of the product to which the polymer is added. Preferably, the dosage ranges from about 0.2 to about 3%, based on the total weight of the composition being treated and most preferably from about 0.5% to about 2.5%, based on the total weight of the composition being treated.

The quaternary diallyl dialkyl ammonium monomer comprises from about 60 to about 99%, based on total polymer weight, while the anionic monomer comprises from about 1 to about 40%, based on total polymer weight. Preferably, the quaternary: anionic weight ratio is from about 95:5 to about 75:25, based on the total weight of polymer. Thus, in the polymers of the present invention, the cationic moiety of the polymer is predominant while the anionic moiety of the polymer is minor. Additionally, other moieties may be present in the instant polymers.

An especially suitable polymer is that where the cationic portion is dimethyldiallyl ammonium chloride (DMDAAC) or diethyldiallyl ammonium chloride (DEDAAC) and where anionic portion is acrylic acid. Preferably, the DMDAAC/DEDAAC:acrylic acid weight ratio weight ratio ranges from about 99:1 to about 60:40, most preferably from about 95:5 to 75:25, based on total polymer weight.

The polymers of the instant invention may have any molecular weight ranging from about 50,000 to about 10,000,000, with the preferred molecular weight ranging from about 200,000 to about 5,000,000. The most preferred viscosity for the instant polymers ranges from about 4,000 to about 10,000 cps, as determined using a Brookfield LVF No. 4 spindle at 60 rpm. These polymers may be prepared using any conventional free radical polymerization technique, such as the technique disclosed by Butler and Angelo, "Journal of American Chemical Society," Vol. 79, p. 3128 (1957) or the technique suggested in U.S. Reissue Pat. No. Re. 28,543. These references are incorporated by reference into this specification.

EXAMPLE 1

The following example is not intended to limit the scope of this invention in any way.

This example demonstrates the use of the instant polymers in anionic personal skin care product formulations.

PEARLESCENT LIQUID SOAP

A liquid soap formulation was prepared using the following ingredients in accordance with the following instructions to demonstrate the excellent compatibility of the instant polymers with anionic surfactants. Compatibility of Merquat 280, which has a net cationic charge density, with an anionic system is surprising and unexpected.

| | Ingredients | % w/w |
|---|---|---|
| A | Deionized Water | 51.90 |
| | Sodium Lauryl Sulfate | 25.00 |
| | Sodium $C_{14-16}$ Olefin Sulfonate[1] | 10.00 |
| | Cerasynt M[2] | 0.40 |
| | Cocamide DEA[3] | 2.00 |
| | Cocamidopropyl Betaine[4] | 8.00 |
| B | MERQUAT 280[5] | 2.00 |
| C | Fragrance | 0.50 |
| | Tetrasodium EDTA[6] | 0.20 |
| D | Citric Acid | to pH 6.00 |
| | Sodium Chloride | to viscosity 2800 cps |

[1]Sodium laureth sulfate is $C_{14-16}$ olefin sulfonate sulfate is an anionic surfactant.
[2]Cerasynt is ethylene glycol monostearate, available from Van Dyk & Co., Inc.
[3]Cocamide DEA is coconut diethanolamine, available from Van Dyk and Co., Inc.
[4]Cocamidopropyl betaine is a coconut amidopropyl betaine.
[5]Merquat 280 is an 80/20 w/w polymer of DMDAAC and acrylic acid having a viscosity (Brookfield LVF #4 spindle @ 30 rpm) of 4,000–10,000 cps, and a weight average molecular weight of approximately 1,300,000, as determined by gel permeation chromatography, commercially available from Calgon Corporation.
[6]Tetrasodium EDTA is the sodium salt of ethlenediamine tetraacetic acid.

Preparation Instructions

Heat water to 75° C. With moderate agitation, add the ingredients listed in Part A in the order stated proceeding after each addition is uniform. Begin cooling and add MERQUAT 280 at 50° C. Continue mixing and cooling and add Part C at 45° C. Adjust pH to 6.0 with citric acid. Add sodium chloride to increase viscosity to 2800 cps. Optionally, fragrances and dyes can be added.

What is claimed is:

1. A method for improving feel imparted to skin by a personal skin care product comprising adding to said product an effective amount of a polymer comprising:
    a. about 60 to about 99%, by weight of said polymer, of a quaternary diallyl dialkyl ammonium monomer, wherein alkyl groups are independently selected from alkyl groups of 1 to 18 carbon atoms and wherein said quarternary diallyl dialkyl ammonium monomer's counterion is selected from the group consisting of bases of acids having an ionization constant greater than $10^{-13}$ b. about 1 to about 40%, by weight of said polymer, of an anionic monomer selected from the group consisting of acrylic acid and methacrylic acid; wherein the weight average molecular weight of said polymer ranges from about 50,000 to 10,000,000, as determined by gel permeation chromatography.

2. The method of claim 1, wherein said alkyl group of (a) is $C_{1-4}$.

3. The method of claim 1, wherein (a) is selected from the group consisting of dimethyldiallyl ammonium chloride and diethyldiallyl ammonium chloride and (b) is acrylic acid.

4. The method of claim 1, wherein said effective amount ranges from about 0.1 to about 5%, by weight, of said product.

5. The method of claim 1, wherein said product comprises an active agent and a surfactant.

6. The method of claim 5, wherein said surfactant is anionic.

7. The method of claim 1, wherein said counterion is selected from the group consisting of fluoride, chloride, bromide, hydroxide, nitrate, acetate, hydrogen sulfate and primary phosphates.

8. An improved personal skin care product which comprises:
   a. an active agent;
   b. an anionic surfactant;
   c. a copolymer comprising;
      1. about 60 to about 99%, by weight of said polymer, of a monomer selected from the group consisting of dimethyldiallyl ammonium chloride and diethyldiallyl ammonium chloride; and
      2. about 1 to about 30%, by weight of said polymer, a momomer selected from the group consisting of acrylic acid, and methacrylic acid; wherein said polymer has a weight average molecular weight ranging from about 50,000 to about 10,000,000, as determined by gel permeation chromatography.

* * * * *